United States Patent [19]

Ryang

[11] Patent Number: 4,892,918

[45] Date of Patent: Jan. 9, 1990

[54] SECONDARY AMINE TERMINATED SILOXANES, METHODS FOR THEIR PREPARATION AND USE

[75] Inventor: Hong-Son Ryang, Camarillo, Calif.

[73] Assignee: BASF Corporation, Parsippany, N.J.

[21] Appl. No.: 55,312

[22] Filed: May 29, 1987

[51] Int. Cl.$^4$ .............................................. C08G 77/06
[52] U.S. Cl. ..................................... 528/15; 525/103; 525/479; 525/523; 528/28; 528/31; 528/33; 528/37; 528/38; 556/425; 556/462; 556/479
[58] Field of Search ....................... 556/425, 462, 479; 528/28, 31, 15, 33, 37, 38; 525/523, 103, 479

[56] References Cited

U.S. PATENT DOCUMENTS

| 3,146,250 | 8/1964 | Speier | 556/425 |
| 3,170,941 | 2/1965 | Speier | 556/425 |
| 4,645,614 | 2/1987 | Goossens et al. | 528/38 |

OTHER PUBLICATIONS

Noll, Chemistry and Technology of Silicones, Academic Press, New York, pp. 9–16 (1968).

*Primary Examiner*—Melvyn J. Marquis
*Attorney, Agent, or Firm*—William G. Conger

[57] ABSTRACT

Secondary-amino-functional organosilicone are prepared by the reaction of an N-substituted, secondary allylamine with an Si-H functionalized organosilicone particularly a di- or polysiloxane. The resulting products are useful in toughening thermosetting matrix resins, particularly epoxy resins.

16 Claims, No Drawings

SECONDARY AMINE TERMINATED SILOXANES, METHODS FOR THEIR PREPARATION AND USE

BACKGROUND OF THE INVENTION

1. Field of the Invention

The subject invention relates to novel secondary amine-terminated siloxanes, and to a novel and efficient process for their preparation. These products are useful in polymer preparation and modification, and in particular, as difunctional amine curing agents for epoxy and other aminereactive resins.

2. Description of the Related Art

Epoxy resins are widely used in fabricating structures, in particular as adhesives and as matrix resins in heat curable, thermosetting, fiber-reinforced composites. Epoxy resins are suitable for such applications because of their excellent physical properties. However, epoxy resins which maintain high tensile strengths at elevated temperatures, such as the amine cured polyglycidyl derivatives of p-aminophenol or 4,4'-methylenedianiline, tend to be somewhat brittle. Thus, while their high tensile strengths make them particularly compatible with high strength fibers such as carbon/graphite, glass, aramid, and polyethylene, their brittle nature causes them to be subject to considerable impact-induced damage.

Epoxy resins used as adhesives are generally of lower functionality and/or higher equivalent weight, and therefore have less cross-linking density and lower tensile strength that their higher-functionality, matrix-resin kindred. However, even here, increased resistance to impact damage would be desirable.

Functionalized elastomers such as the amino- or carboxy-terminated butadiene-acrylonitrile copolymers (ATBN and CTBN, respectively) available from B.F. Goodrich Corp. under the trademark HYCAR® have been used with some degree of success in toughening both adhesive and matrix resin formulations. See, for example, the article by J. Riffle, et. al., entitled "Elastomeric Polysiloxane Modifiers" in *Epoxy Resin Chemistry II*, R. Bauer, Ed., ACS Symposium Series No. 221, American Chemical Society, and the references cited therein.

The use of ATBN elastomers having carbon backbones containing unsaturation, while increasing toughness, does not provide sufficient thermal and/or oxidative stability for many modern applications of adhesives and matrix resins, particularly those in the aerospace field. Thus it has been proposed to utilize functionalized polysiloxanes for these applications, relying on the thermal-oxidative stability of the silicon-containing backbone to lend increased thermal stability to the total resin system. Several such approaches have been discussed in Riffel, supra, and involve primary amine terminated polysiloxanes such as bis(3-aminopropyl)polysiloxanes and secondary amine terminated polysiloxanes such as bis(piperazinyl)polysiloxanes.

Perhaps due to their lower functionality, the secondary amine terminated, piperazinyl polysiloxanes generally proved to have superior physical properties than the primary amine terminated polysiloxanes (tetrafunctional). Unfortunately, these secondary amine terminated polysiloxanes are difficult to prepare.

One preparation of piperazinyl functionalized polysiloxanes involves reaction of 2-aminoethyl piperazine with a previously synthesized carboxy-terminated polysiloxane to form the bis(2-piperazinyl ethyl amide) of the polysiloxane:

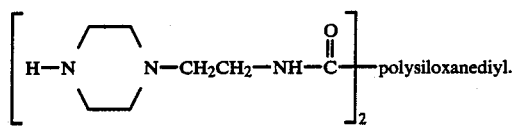

A second approach is to react a large excess (to avoid polymer formation) of piperazine with a bis-epoxy polysiloxane, producing a bis(2-hydroxy-3-piperazinyl) polysiloxane:

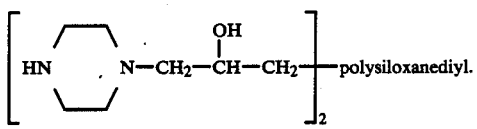

This method, of course, requires prior preparation of the epoxy-functional polysiloxane.

Ryang, in U.S. Pat. No. 4,511,701, prepared both primary and secondary amine-terminated polysiloxanes by reacting an appropriately substituted diamine with difunctional silylnorbornane anhydrides, themselves prepared as disclosed by Ryang in U.S. Pat. No. 4,381,396. Reaction of these diamines with the bis(anhydride) functional polysiloxanes results in amino-imides such as:

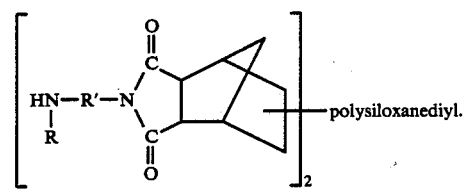

Only the last-mentioned process produces amino-functional polysiloxanes which are truly difunctional. The amide hydrogen and hydroxyl hydrogen produced by the first two preparations, though less reactive than the secondary amino hydrogens, are nevertheless reactive species in most resin systems. Their presence, therefore can cause further, and at times unpredictable cross-linking, either over an extended period of time in normal service, or as a result of high curing temperatures.

Furthermore, all of the foregoing preparations involve many steps, and in the process consume large quantities of relatively expensive chemical reagents. All these prior art products are difficult to prepare, expensive products, and thus there remains a need for thermally stable, secondary amine terminated polysiloxanes which may be prepared in high yield and in an economic manner.

SUMMARY OF THE INVENTION

It has now been surprisingly discovered that novel secondary amine-functionalized organosilicones may be readily prepared in quantitative or nearly quantitative yields, by reacting a secondary N-allylamine corresponding to the formula:

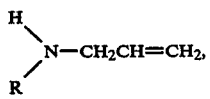

or an analogous secondary N-(γ-butenyl)- or N-(δ-pentenyl)amine with an Si–H functional organosilicone, preferably a 1,1,3,3-tetrasubstituted disiloxane or silane functional persubstituted polysiloxane, in the presence of a suitable catalyst. In the disclosure which follows, references to the reaction of secondary N-allylamines should be taken to include, where appropriate, the corresponding reaction of secondary-N-(γ-butenyl)amines and secondary-N-(δ-pentenyl)amines. In the structural formulas presented herein, the "V" radical, , represents a divalent n-propyl (propylene) radical. Higher molecular weight polysiloxanes may be prepared by the equilibrium polymerization of the product of the above reaction with additional siloxane monomer to form secondary amine-functionalized homopolymers of higher molecular weight, or block or heteric organosilicones which correspond to the general formula

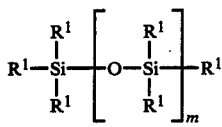

wherein each $R^1$ may be individually selected from the group consisting of alkyl, preferably $C_1$–$C_{12}$ lower alkyl; alkoxy, preferably $C_1$–$C_{12}$ lower alkoxy; acetoxy; cyanoalkyl; halogenated alkyl; and substituted or unsubstituted cycloalkyl, aryl, and aralkyl;

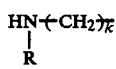

wherein k is an integer from 3 to about 5, preferably

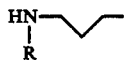

and X, wherein X is selected from the group consisting of

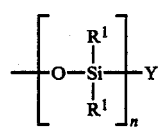

wherein Y is selected from the group consisting of alkyl, preferably $C_1$–$C_{12}$ lower alkyl; alkoxy, preferably $C_{1-C12}$ lower alkoxy; acetoxy; cyanoalkyl; halogenated alkyl; cycloalkyl; aryl; and araalkyl; wherein m is a natural number from 0 to about 10,000, preferably from 1 to about 500; wherein n is a natural number such that the sum of m+n is from about 0 to 10,000, preferably from 1 to about 1000, and more preferably from 1 to about 500; and wherein at least one of $R^1$, X, or Y is

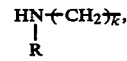

wherein k is an integer from 3 to about 5. Most preferably, the secondary amino functional organosilicones are bis[secondary ω-amino-functionalized] organosilicones which correspond to the formula

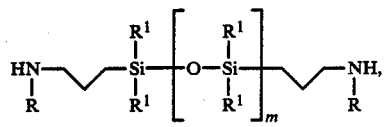

where R may be a substituted or unsubstituted alkyl, cycloalkyl, aryl, or aralkyl group which does not carry a primary amino group, and where each $R^1$ may be individually selected from cyano, alkyl halogenated alkyl, preferably $C_1$–$C_{12}$ lower alkyl, alkoxy, preferably $C_1$–$C_{12}$ lower alkoxy, acetoxy, cycloalkyl, aryl, or aralkyl groups, and wherein m is an integer from 0 to about 10,000, preferably 1 to about 500.

As indicated, the $R^1$ substituents may be the same as each other, or may be different. The phrase "may be individually selected," or similar language as used herein, indicates that individual $R^1$s may be the same or different from other $R^1$ groups attached to the same silicon atom, or from other $R^1$ groups in the total molecule. Furthermore, the carbon chain of the ω-aminoalkylene-functional organosilicone may be substituted by inert groups such as alkyl, cycloalkyl, aryl, arylalkyl, and alkoxy groups. References to secondary aminopropyl, aminobutyl, and aminopentyl groups include such substituted ω-aminoalkyl groups.

In addition to the preferred bis(N-substituted, secondary aminopropyl)polysiloxanes, tris- or higher analogues may also be prepared by the subject process if branched or multi-functional siloxanes are utilized. Such higher functionality secondary amino-functionalized siloxanes, for example, may be useful as curing agents with resins of lesser functionality. Monofunctional N-substituted, secondary 4-aminobutyl-, 5-aminopentyl, and 3-aminopropylsiloxanes may also be prepared. Such monofunctional siloxanes have uses as reactive modifiers in many polymer systems.

DESCRIPTION OF THE PREFERRED EMBODIMENTS

The secondary-amine-functional organosilicones of the subject invention may be prepared through the reaction of an N-allyl secondary amine with an Si–H functional organosilicone. In the discussion which follows, references to organosilicone reactants, in general, are intended to include silanes and diand polysiloxanes which have Si–H functionality. The preferred reaction may be illustrated as follows:

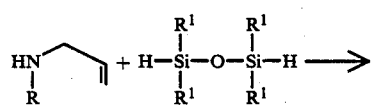

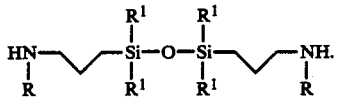

Of course, by varying the nature of the Si-H functional organosilicone, a variety of products may be obtained. For example, a polysiloxane having one or more pendent secondary amino functionalities may be prepared readily from an Si-H functional cyclic siloxane;

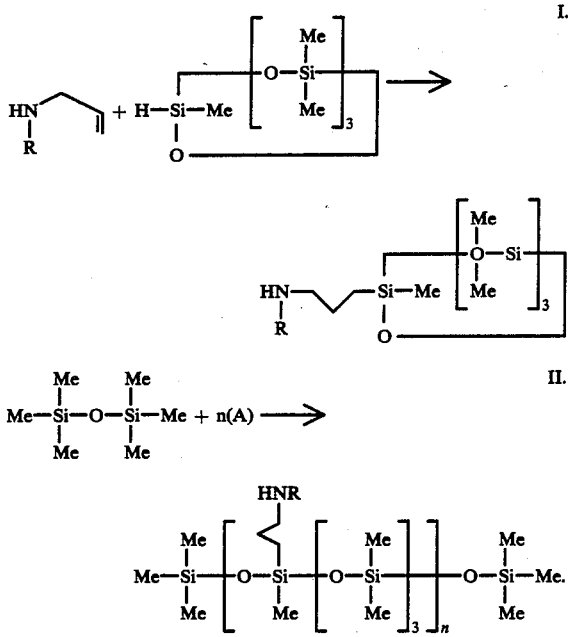

A wide variety of allylamines and corresponding γ-butenyl and δ-pentenylamines are useful in this synthesis. However, as is well known, amines such as the secondary alkylamines, for example dimethylamine and dipropylamine, as well as (primary) allylamine itself, fail to react in a satisfactory and reproducible manner. For example, U.S. Pat. No. 3,665,027 discloses the reaction of allylamine with a monofunctional hydrogen alkoxysilane. Despite the presence of the activating alkoxy groups and exceptionally long reaction times, the reaction provided at most an 85 percent yield. Furthermore, the reaction produces considerable quantities of potentially dangerous peroxysilanes as by-products. For these reasons, the preparation disclosed is not a desirable one for producing even monofunctional γ-aminopropyl trialkoxy siloxanes. Attempts to utilize the reaction for the preparation of higher functionality siloxanes, particularly alkyl-substituted siloxanes such as the poly(dimethyl)silicones, have not proven successful. It is also known that use of vinylamine leads only to intractable products of unspecified composition.

One reason that such processes produce poor and irreproducible results is the well known fact that primary amines poison platinum catalysts. The greater amount of amine present per mole of catalyst, the greater the degree of catalyst alteration. Thus where an amine such as allylamine or vinylamine is added in mole-to-mole correspondence with the hydrogen functionality of the hydrogen functional organosilicone, the expected catalyst function is disrupted and numerous side reactions, including polymerization of the vinyl or allyl compounds may occur. Thus it is necessary that the amine be a secondary, N-allylamine or secondary, N-(unsaturated alkylamine) wherein the double bond is located at least two carbons from the secondary amino nitrogen.

In the list of suitable secondary alkylamines which follows, it should be noted that the corresponding γ-butenyl and δ-pentenylamines are also suitable. Examples of amines which are suitable, include N-alkyl-N-allyl amines such as N-methyl, N-ethyl, N-propyl, N-isopropyl, N-butyl, N-isobutyl, N-tert-butyl, and N-(2-ethylhexyl)allylamines and the like; cycloaliphatic-N-allylamines such as N-cyclohexyl, N-(2-methylcyclohexyl), and N-(4-methylcyclohexyl)-N-allylamines; aliphatic cycloaliphatic-N-allylamines such as N-cyclohexylmethyl and N-(4-methylcyclohexylmethyl)-N-allylamines; aralkyl (aromatic-aliphatic)-N-allylamines such as N-benzyl, N-(4-methylbenzyl), N-(2-methylbenzyl), and N-(4-ethylbenzyl)-N-allylamines; and aryl (aromatic)-N-allylamines such as N-phenyl, N-(4-methylphenyl), N-(4-nonylphenyl), and N-naphthyl-N-allylamines; and aromatic N-allylamines where the aromatic component has the formula

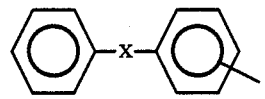

Where X is

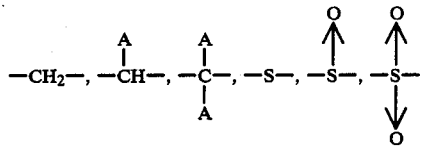

and 0, and where A is $C_1$-$C_6$ lower alkyl.

While these and many other N-allyl secondary amines are useful for the practice of the subject invention, it must be recognized that some are more preferred than others. In general, the cycloaliphatic and aryl-N-allylamines are preferred. Particularly preferred are N-cyclohexyl-N-allylamine and N-phenyl-N-allylamine. It should be noted that the secondary N-allyl amines are more preferred than their γ-butenyl and δ-pentenyl analogues.

As the Si-H functional organosilicone may be used compounds of the formulas:

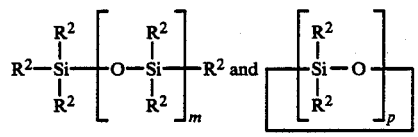

wherein $R^2$ is selected from the group consisting of hydrogen; alkyl, preferably $C_1$-$C_{12}$ lower alkyl; alkoxy, preferably $C_1$-$C_{12}$ lower alkoxy; acetoxy; cyanoalkyl; halogenated alkyl, preferably perhalogenated alkyl; and substituted or unsubstituted cycloalkyl, aryl, or araalkyl; and

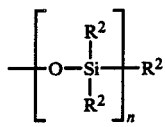

wherein m and n are natural numbers from 0 to about 10,000, preferably from 0 to about 500 and more preferably from 1 to about 100; wherein p is a natural number from 3 to about 20, preferably from 4 to about 8; and wherein the sum n+m is less than about 10,000, preferably less than about 500, more preferably less than about 100; and wherein at least one $R^2$ is hydrogen. Most preferably, the Si-H functional organosilicone is an Si-H functional disiloxane, preferably

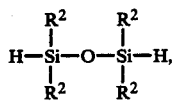

where $R^2$ is cyanoalkyl, halogenated alkyl, alkyl, alkoxy, cycloalkyl, or aryl. Examples of such Si-H functional organosilicones are trimethoxy- and triethoxysilane, tetramethyldisiloxane, tetraethyldisiloxane, 1,1,3,3,5,5-hexamethyltrisiloxane, methyltris(dimethylsiloxysilane), 1,1,3,3,5,5,7,7-octamethyltetrasiloxane, tetramethoxydisiloxane, tetraethoxydisiloxane, 1,1-bis(-trifluoropropyl)-3,3-dimethyldisiloxane, pentamethylcyclopentasiloxane, heptamethylcyclotetrasiloxane, tetramethylcyclotetrasiloxane, methylhydrosiloxane-dimethylsiloxane copolymers, and tetraphenyldisiloxane. Particularly preferred because of its low cost and ready availability is tetramethyldisiloxane. Mixed-substituted alkyl-aryl siloxanes such as 1,3-dimethyl-1,3-diphenyldisiloxane are also useful.

The N-allyl secondary amine and Si-H functional organosilicone are preferably reacted neat, in the absence of solvent. However solvents which are inert under the reaction conditions may be utilized if desired. The use of solvent may affect both the average molecular weight of the product polysiloxane and the molecular weight distribution.

The reaction temperature is preferably maintained between about 20° C. and 150° C. depending upon the nature and amount of catalyst and reactants. A catalyst is generally necessary to promote reaction between the amine and the Si-H functional organosilicone. Surprisingly, it has been found that even rather inefficient catalysts such as hexafluoroplatinic acid and hexachloroplatinic acid are highly effective, frequently resulting in quantitative yields. Other catalysts which are useful include those well known in the art, typically platinum catalysts in which the platinum is present in elemental or combined states, particularly di- or tetravalent compounds. Useful catalysts are, for example, platinum supported on inert carriers such as aluminum or silica gel; platinum compounds such as $Na_2PtCl_4$, $K_2PtCl_4$, and the previously mentioned platinic acids, particularly hexachloro- and hexafluoroplatinic acids. Also useful are alkylplatinum halides; siloxyorganosulfur-platinum or aluminoxyorganosulfurplatinum compositions, and those catalysts prepared through the reaction of an olefinic-functional siloxane with a platinum compound as disclosed in U.S. Pat. Nos. 3,419,593; 3,715,334; 3,814,730; and 4,288,345. Other catalysts may also be effective, such as those found in U.S. Pat. No. 3,775,452. All the foregoing U.S. Patents are herein incorporated by reference. However, because of its (relatively) low cost and the high yields it produces, hexachloroplatinic acid is the catalyst of choice.

Purification of the secondary amine-functionalized organosilicone product is accomplished by methods well known to those skilled in the art of purifying silicones. Generally, vacuum distillation is utilized, for example distillation at pressures less than about 1 torr. In some cases, purification may be effectuated by stripping off light fractions under vacuum, optionally with the aid of an inert stripping agent such as nitrogen or argon.

The secondary amine-functionalized organosilicones may be utilized as such, or they may be further polymerized with additional silicon-containing monomers to produce higher molecular weight secondary amine-functionalized polysiloxanes. For example, a secondary amine-functionalized tetramethyl disiloxane may be converted easily to a secondary amine-terminated poly(dimethylsiloxane) by equilibration with octamethylcyclotetrasiloxane:

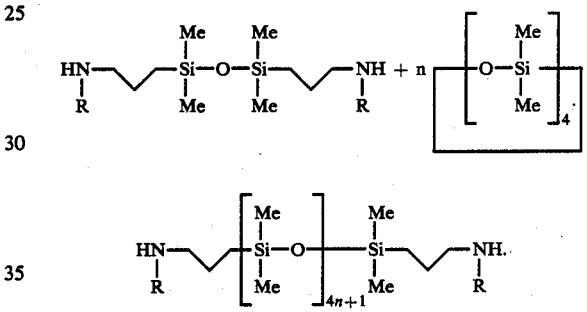

The equilibration co-polymerization is facilitated through the use of catalysts well known to those skilled in the art. A particularly useful catalyst which is relatively inexpensive and readily available is tetramethylammonium hydroxide. However, many other catalysts are also suitable, such as potassium hydroxide, cesium hydroxide, tetramethylammonium siloxanolate, and tetrabutylphosphonium hydroxide, which are also preferred.

If copolymer polysiloxanes are desired, then a different siloxane comonomer may be added to the reaction mixture. For example, a secondary amine-terminated tetramethyldisiloxane may be reacted on a mole to mole basis with octaphenylcyclotetrasiloxane to produce a copolymer polysiloxane having the nominal formula:

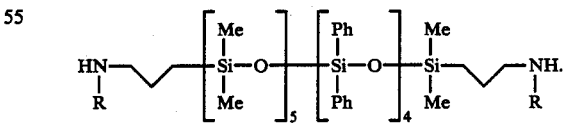

Or, in the alternative, the secondary amine-terminated disiloxane or polysiloxane may be reacted with mixtures of siloxane monomers to form block and block heteric structures.

The secondary amine-terminated polysiloxanes of the subject invention have a wide variety of uses including toughening adhesives, matrix resin formulations, potting compounds, coatings, encapsulants, and the like.

The high thermal stability of these compounds makes them especially useful in elevated temperature applications.

The subject invention may be illustrated by the following preparative examples, which should not be considered as limiting in any way. All reagent quantities are by weight or by gram-mole, as indicated.

EXAMPLE 1

Synthesis of 1,3-bis(N-phenyl-3-aminopropyl)-1,1,3,3-tetramethyldisiloxane.

N-allylaniline (0.200 mole) and 1,1,3,3-tetramethyldisiloxane (0.100 mole) are introduced along with 0.05 g hexachloroplatinic acid into a 100 ml cylindrical glass reactor equipped with reflux condenser, nitrogen inlet, and stir bar. The contents of the reaction are heated and maintained while stirring, at approximately 70° C., for a period of ten hours. The IR spectrum of the resulting viscous oil shows no peaks corresponding to Si-H, indicating completion of the reaction. The crude product is mixed with carbon black and stirred overnight at room temperature. The product is filtered through silica gel and the filter cake washed with toluene. Volatile fractions are removed by stripping under vacuum at 150° C. to give a slightly colored oil. The oil is further purified by vacuum distillation at <1 torr at 223°–230° C. The yield of 1,3-bis(N-phenyl-3-aminopropyl)-1,1,3,3-tetramethyldisiloxane is virtually quantitative.

EXAMPLE 2

Synthesis of 1,3-bis(N-cyclohexyl-3-aminopropyl)-1,1,3,3-tetramethyldisiloxane.

Following the technique described in Example 1, N-allylcyclohexylamine (0.173 mole), 1,1,3,3-tetramethyldisiloxane (0.0783 mole), and 0.05 g hexachloroplatinic acid are stirred at 70° C for eight hours at 110° C. under nitrogen. The product, in nearly quantitative yield, is purified by vacuum distillation at <1 torr at a temperature of 207°–210° C.

EXAMPLE 3

Synthesis of α,ω-bis(N-phenyl-3-aminopropyl)-polysiloxane copolymer.

Into a 500 ml glass reactor equipped with a reflux condenser, mechanical stirrer, and nitrogen inlet are introduced 1,3-bis(N-phenyl-3-aminopropyl)-1,1,3,3-tetramethyldisiloxane (0.100 mole), octamethylcyclotetrasiloxane (0.270 mole), octaphenylcyclotetrasiloxane (0.100 mole), and tetramethylammonium hydroxide (0.3 g). The reaction mixture is stirred at 80° C. for 44 hours followed by an additional 4 hours at 150° C., all under nitrogen. The resultant viscous oil is filtered and volatiles removed under vacuum at 300° C. The resulting copolymer is obtained in high yield as a slightly colored viscous oil.

EXAMPLE 4

Synthesis of α,ω-bis(N-cyclohexyl-3-aminopropyl capped polysiloxane copolymer.

Utilizing the procedure of Example 3, 1,3-bis(N-cyclohexyl-3-aminopropyl)-1,1,3,3-tetramethyl disiloxane (0.0485 moles), octamethylcyclotetrasiloxane (0.179 moles), octaphenylcyclotetrasiloxane (0.067 mole) and tetramethylammonium siloxanolate (1.20 g) are allowed to react over a period of 40 hours at 90° C. and an additional 4 hours at 150° C. After cooling to room temperature, the filtered reaction mixture is vacuum stripped at <1 torr and 250° C. to yield a viscous oil in high yield.

EXAMPLE 5

Using the procedure of Example 1, N-allylaniline (0.10 mole), a cogeneric mixture of —(Me$_2$)Si-H terminated polydimethylsiloxanes having an average molecular weight of approximately 1200 Daltons (0.050 mole), and hexachloroplatinic acid (0.03 g) are stirred at 90° for 10 hours and 150° for 8 hours. Following filtration and vacuum stripping at less than 1 torr, the resulting bis(N-phenyl-3-aminopropyl) polydimethylsiloxane is isolated as a viscous oil.

EXAMPLE 6 AND COMPARATIVE EXAMPLE

The secondary-amino-functionalized silicone of Example 3 (30.0 g); a trifunctional epoxy resin which is the glicidyl ether of tris(4-hydroxyphenyl)methane (Tactix ® 742, available from the Dow Chemical Company, Midland, Mich.)(33.75 g); and a lower functional epoxy resin which is the glicidyl ether of bisphenol A (DER ® 332, available from Dow Chemical) (11.25 g) were charged into a 250 ml glass reactor. The reaction mixture was stirred at 140° C. for two hours under nitrogen. The resulting product, Resin A, was a viscous, opaque but homogenous oil.

Two thermosetting resin formulations were prepared, with and without the incorporation of toughened epoxy prepared as described above. The samples were cured at 177° C. for four hours followed by a 220° C. postcure for an additional four hours. The cured resin plaques were homogenous opaque solids. The plaques were tested for thermal stability by Thermogravimetric Analysis (TGA). The respective formulations and TGA results are given below in Table I. The results indicate that the secondary amino functionalized organosilicones, when used to toughen epoxy formulations, does not cause a decrease in thermal stability as in the case when CTBN, ATBN, or similar toughening modifiers are utilized.

TABLE I

| | Resin Composition[1] | | | | TGA, °C. in Air | | |
|---|---|---|---|---|---|---|---|
| | Toughener (Resin A) | Tactix ® 742 | DER 332 | 3,3'-DDS[2] | 2% Wt. Loss | 5% Wt. Loss | 10% Wt. Loss |
| Example 6 | 1.68 | 1.33 | 0.29 | 1.00 | 386 | 400 | 410 |
| Comparative Example | | 3.75 | 1.25 | 1.80 | 386 | 390 | 410 |

[1]All quantities in grams
[2]3,3'-diaminodiphenylsulfone

The embodiments of the invention in which an exclusive property or privilege is claimed are defined as follows:

1. A process for the preparation of a secondary amine-functionalized organosilicone, comprising reacting (a) an N substituted-N-alkenylmonoamine selected from the group consisting of N-aryl-N-alkenyl amines, N-alkyl-N-alkenylamines, N-cycloalkyl-N-alkenyl amines, and N-aralkyl-N-alkenyl amines, wherein the ethylenic unsaturation of said alkenyl amine is located at least two carbon atoms away from the amino nitrogen, with:

(b) an Si-H functional organosilicone selected from the group consisting of

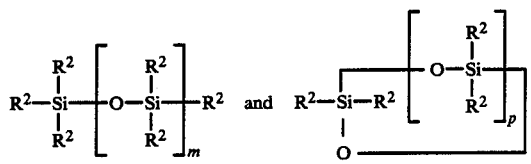

where each $R^2$ is selected from the group consisting of hydrogen; alkyl; alkoxy; cyanoalkyl; halogenated alkyl; acetoxy; and substituted and unsubstituted cycloalkyl, aryl, and aralkyl; and

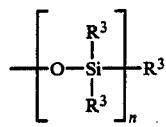

wherein m and n are natural numbers from 1 to about 10,000; wherein p is a natural number from 2 to about 20; wherein the sum m+n is less than about 10,000; wherein $R^3$ is selected from the group consisting of hydrogen; alkyl alkoxy; cyanoalkyl; halogenated alkyl; acetoxy; and substituted and unsubstituted cycloalkyl, aryl, and aralkyl; and wherein at least one of $R^2$ or $R^3$ is hydrogen; in the presence of, (c) a hydrosilation reaction-promoting-catalyst present in an amount effective to catalyze the reaction between (a) and (b).

2. The process of claim 1 wherein said organosilicone is selected from the group consisting of:

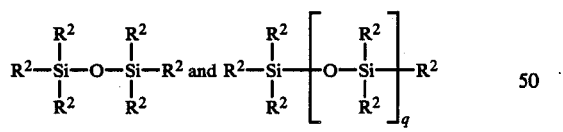

where q is an integer from 2 to about 100.

3. The process of claim 2 wherein said catalyst is selected from the group consisting of hexafluoroplatinic acid and hexachloroplatinic acid and the hydrates and salts thereof.

4. The process of claim 2 wherein each $R^2$ is individually selected from the group consisting of hydrogen, methyl, ethyl, and phenyl.

5. The process of claim 2 wherein said organosilicone is selected from the group consisting of tetramethyldisiloxane, tetraphenyldisiloxane, and 1,3-dimethyl-1,3-diphenyldisiloxane.

6. The process of claim 2 wherein said organosilicone is an Si-H terminated cogeneric polydimethylsiloxane corresponding to the formula:

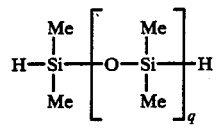

wherein q is an integer from about 1 to about 10,000.

7. The process of claim 1 said N-substituted-N-alkenyl monoamine is an N-alkyl or N-aryl-N-allyl monoamine.

8. A process for the preparation of an N-substituted, secondary ω-aminoalkyl organosilicone polymer, comprising:

(a) preparing an N-substituted, secondary ω-aminoalkyl functionalized organosilicone having the formula:

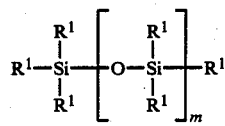

by the process of claim 1, wherein $R^1$ is individually selected from the group consisting of alkyl, alkoxy; cycloalkyl, halogenated alkyl; acetoxy; and substituted and unsubstituted cycloalkyl, aryl, and araalkyl;

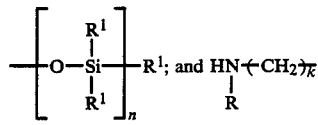

wherein k is an integer from 3 to about 5;
wherein n is a natural number from 0 to about 10,000;
wherein m is a natural number from 0 to about 10,000;
wherein the sum m+n is less than about 10,000; and
wherein at least one $R^1$ is

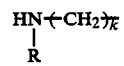

wherein R is selected from the group consisting of substituted and unsubstituted alkyl, cycloalkyl, aryl and araalkyl radicals carrying no primary amino groups;

(b) reacting the (N-substituted, secondary ω-aminoalkyl functionalized organosilicone (a) with one or more persubstituted cyclosiloxanes having the formula:

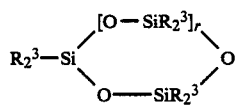

wherein r is an integer from 1 to about 10, and $R^3$ is selected individually from the group consisting of acetoxy, alkyl, alkoxy, cyanoalkyl, halogenated alkyl, cycloalkyl, aryl, and aralkyl radicals; in the presence of (c) an effective amount of polysiloxane equilibration-polymerization catalyst, to form a higher molecular weight N-substituted, secondary ω-aminoalkyl organosilicone.

9. The process of claim 8 wherein said N-substituted, secondary ω-aminoalkyl functionalized organosilicone is an N-substituted, secondary 3-aminopropyl functionalized organosilicone.

10. The process of claim 9 wherein said cyclosiloxane is selected from the group consisting of octamethylcyclotetrasiloxane, octaphenylcyclotetrasiloxane, 1,2,3,4-tetramethyl-1,2,3,4-tetraphenylcyclotetrasiloxane, hexamethylcyclotrisiloxane, hexaphenylcyclotrisiloxane, and 1,2,3-trimethyl-1,2,3-triphenylcyclotrisiloxane.

11. The process of claim 9 wherein said cyclosiloxane is selected from the group consisting of octamethylcyclotetrasiloxane and octaphenylcyclotetrasiloxane.

12. The process of claim 9 wherein said polymerization catalyst is selected from the group consisting of the alkali metal silanolates and siloxanolates; the tetrakis(alkyl)ammonium silanolates and siloxanolates; tetrakis(alkyl)phosphonium silanolates and siloxanolates; tetrakis(alkyl)phosphonium hydroxides; and the tetrakis(alkyl)ammonium hydroxides.

13. The process of claim 9 wherein said polymerization catalyst is selected from the group consisting of tetramethylammonium hydroxide and tetramethylammonium siloxanolate.

14. In a process for toughening heat-curable thermosetting resins, the improvement comprising incorporating into said thermosetting resin a roughening amount of a secondary ω-amino alkyl-functionalized organosilicone prepared by the process of claim 1.

15. In a process for toughening heat-curable thermosetting resins, the improvement comprising incorporating into said thermosetting resin a toughening amount of the N-substituted, secondary ω-aminoalkyl organosilicone prepared by the process of claim 8.

16. The process of claim 14 wherein said thermosetting resin comprises a resin selected from the group consisting of epoxy resins, bismaleimide resins, cyanate resins, and mixtures thereof.

* * * * *